United States Patent [19]

Hüttenrauch

[11] 4,315,909
[45] Feb. 16, 1982

[54] PROCESS FOR THE PREPARATION OF SOLID DRUG FORMULATIONS

[75] Inventor: Reinhard Hüttenrauch, Jena, German Democratic Rep.

[73] Assignee: Veb Jenapharm, Jena, German Democratic Rep.

[21] Appl. No.: 81,449

[22] Filed: Oct. 3, 1979

Related U.S. Application Data

[63] Continuation-in-part of Ser. No. 78,200, Sep. 24, 1979, abandoned.

[30] Foreign Application Priority Data

Sep. 25, 1978 [DD] German Democratic Rep. ... 208050

[51] Int. Cl.$^3$ .............................................. A61K 9/34
[52] U.S. Cl. .................................... 424/35; 424/247; 424/274; 424/326
[58] Field of Search ................. 424/35, 247, 274, 326

[56] References Cited

U.S. PATENT DOCUMENTS 4,115,537 9/1978 Driscoll et al. ...................... 424/14

OTHER PUBLICATIONS

The Merck Index, Ninth Edition, pp. 4073, 7019, 7234, (1976).
Gutbauer et al., Osterr., Chemiker Zeitung, vol. 67 (10), pp. 349–361, (1966).
Drawe, Angewandte Strahlenchemie, pp. 63–82, Dr. Huthig-Verlag Heidelberg, (1973).

*Primary Examiner*—Alan L. Rotman
*Attorney, Agent, or Firm*—Michael J. Striker

[57] ABSTRACT

In order to allow for the greatest possible range of variation in the rate of liberation of active agents within an organism and to allow for the use of a wide variety of active agents in solid drug formulations, cellulose graft copolymers are employed as adjuvant. The excellent flow properties and compacting behavior of these cellulose graft copolymers allow for formulation without the need for additional process steps, while variations in the type and proportion of the grafted components allows for the synthesis of adjuvants ideally suited for a specific intended use.

5 Claims, No Drawings

PROCESS FOR THE PREPARATION OF SOLID DRUG FORMULATIONS

This application is a continuation-in-part of Ser. No. 078,200 filed Sept. 24, 1979, now abandoned.

BACKGROUND OF THE INVENTION

The invention concerns a process for the manufacture of solid drug formulations or dosage units, and in particular, a process in which special pharmaceutical adjuvants and additives are used to produce preparations with specific dissolution, disintegration and liberation properties.

In the manufacture of solid drug formulations, it is generally a paramount objective to provide the active agents in such a form that they display certain rates, durations and strengths of activity. Preparation and administration of these active agents is no longer carried out without a consideration of their behavior in the organism. There are known numerous galenic methods which influence the availability of the active agents, as well as the parameters of activity dependent thereon. The effect achieved through the use of such agents may variously be an acceleration or a delay of availability; discontinuous as well as uniform effects may be achieved. The types of processes commonly involved may be subdivided for convenience into those which influence the dissolution rate and those which change the diffusion or permeation rate. A faster liberation of the active agent, for example, may be effected by surface enlargement (e.g. crushing), amorphization or addition of solubilizers; a delayed liberation is made possible by embedding the active agent into or coating it with substances which are only soluble with difficulty.

The present invention is concerned with the development of a novel procedure for delaying the dissolution and thus obtaining a retarding effect. This problem has in principle been dealt with by numerous procedures: methods in which the active agent particles or the whole dosage unit (e.g., tablet, capsule) is located with a film; those in which the active substance is incorporated into an erosive hard fat bed; those in which the active agent is polymerized into a synthetic material; those in which the active agent is pressed or tabletted with a plastic material; and those in which the agent is bound to an insoluble carrier, such as an ion-exchange resin. With each of these procedures, there is either only a limited range of variability or else an additional operational stage in the preparation is required. Moreover, the use of certain matrix-forming agents determines to a large extent the properties of the product units. Other methods, in particular coating processes, require specialized technology.

SUMMARY OF THE INVENTION

It is, therefore, an object of the invention to provide a process which enables the regulation of the course of the liberation of active agents within the organism which does not involve additional formulation steps and which allows for the greatest possible range of variation both in the regulation and in the choice of active agents.

This object is achieved quite simply through the use of cellulose graft polymers as adjuvant. As is generally known in the art, cellulose powders are excellent pharmaceutical adjuvants, especially useful in the manufacture of tablets and hard-gelatin capsules. Their very good flow properties and excellent compacting behavior make them superior to other known materials; thus, for example, it is unnecessary to granulate the cellulose powders prior to tabletting. Through the use of the graft polymerization method, the properties of the cellulose powders may be varied almost at choice. Graft polymerization using various monomers, such as methacrylic esters and styrene, may yield products which, depending upon the structure and proportion of the grafted component, are more than adequate pharmaceutical adjuvants combining the benefits of the cellulose powders, i.e., good flow and compacting behavior, with the properties of synthetic material. The resultant powders may be tabletted directly prior to granulation, as is the case with the starting material. As prestage to the tabletting process, it is only necessary to mix the powders with the active agent or to spray the active agent onto the powders.

While the graft copolymerization process has been used in the surface treatment of cotton and in the preparation of wood items, the material resulting from these known processes could in no way find use in the manufacture of drugs. By starting with cellulose powders suitable for use in the pharmaceutical industry, however, the graft polymerization method, which in general comprises a mixing of the cellulose with suitable monomers and subjecting the mixture to a high-energy irradiation, allows for the preparation of adjuvants whose properties may be varied almost at will.

F. fütlbauer, Österr. Chemiker-Ztf. 67, 1349 (1966) H. Drawe, Angewandte Strahlenchemie, Dr. Hüttif Verlag, Heidelberg 1973.

Liberation of the active agent from the dosage unit or formulation is delayed by the graft copolymers. The adjuvant surface, which has been subjected to a more or less hydrophobic treatment, alters the wettability and the diffusion characteristics of the product. This effect is substantial in hard-gelatin capsules as well as in tablets or dragee cores.

If further modification or decreases are desired, it is possible to use mixture of different graft polymers, or a mixture of graft polymers with cellulose powder or other adjuvants. In no case, however, is further special technology required.

The invention may be better understood through the following examples.

DESCRIPTION OF THE PREFERRED EMBODIMENTS

EXAMPLE 1

Cellulose graft copolymer is mixed with 1% active agent and processed at a compacting pressure of 15 kN/cm$^2$ to yield tablets 11 mm in diameter and 200 mg in weight. In dependence upon the degree of grafting, the tablets exhibit the following properties:

| Sample | cellulose graft copolymer using: | | | ultimate crushing strength | rate of disintegration |
|---|---|---|---|---|---|
| | cellulose | styrene | acrylonitrile | | |
| 0 | 100 | — | — | more than 15 kp | 15 sec |
| 1 | 100 | 10 | 7 | 3.8kp | 90 min |
| 2 | 100 | 25 | 17 | 4.9kp | 180 min |
| 3 | 100 | 50 | 33 | 4.8kp | 150 min |

EXAMPLE 2

Cellulose graft copolymer of sample 3 from Example 1 is mixed with active agent and with different amounts of cellulose powder and processed into tablets as described in the foregoing example. The tablets exhibit the following properties:

| Ratio of cellulose graft copolymer of sample (3): cellulose powder | ultimate crushing strength | rate of disintegration |
| --- | --- | --- |
| 1:9 | 10.0 kp | 54 sec |
| 2:8 | 9.4 kp | 61 sec |
| 3:7 | 8.0 kp | 74 sec |
| 5:5 | 6.4 kp | 78 sec |
| 6:4 | 5.1 kp | 100 sec |

EXAMPLE 3

Cellulose graft copolymer of sample 3 from Example 1 is mixed with cellulose powder in the ratio of 3:7 and thereafter with 1% active substance; the mixture is then processed into tablets under varying compacting pressures as in Example 1. The tablets exhibit the following properties:

| Compacting pressure ($kN/cm^2$) | ultimate crushing strength (kp) | rate of disintegration (sec) |
| --- | --- | --- |
| 5 | 2.8 | 21 |
| 10 | 5.5 | 49 |
| 15 | 8.1 | 78 |
| 20 | 9.4 | 100 |

The cellulose graft copolymers can also be used in the manufacture of granulates and coated tablets.

EXAMPLE 4

50 kg of phenformin hydrochloride (phenylethyl biguanide) is mixed with 199.5 kg of cellulose-styrene graft copolymer and 0.5 kg of magnesium stearate and subsequently compacted to tablets 12 mm in diameter and 250 mg in weight.

EXAMPLE 5

15 kg of pindolol is mixed with 184.6 kg of cellulose-polymethacryl graft copolymer and 0.4 kg magnesium stearate and subsequently compacted to tablets 11 mm in diameter and 200 mg in weight.

EXAMPLE 6

6 kg of fluphenazine hydrochloride is mixed with 93.8 kg of cellulose-styrene graft copolymer and 0.2 kg magnesium stearate and processed into tablets 6 mm in diameter and 100 mg in weight.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. In a process for preparing solid drug formulations, including dosage unit amounts of an active agent and adjuvant, the improvement comprising using a cellulose graft copolymer as 30–100% of said adjuvant.

2. A process as defined in claim 1, wherein said active agent or agents is mixed with said cellulose graft copolymer.

3. A process as defined in claim 1, wherein said active agent is sprayed onto said cellulose graft copolymer.

4. A process as defined in claim 1, wherein said cellulose graft copolymer is used in a mixture with cellulose powder.

5. A process as defined in claim 1, wherein a mixture of cellulose graft copolymers is used.

* * * * *